United States Patent [19]

Kaanta et al.

[11] Patent Number: 4,793,895

[45] Date of Patent: Dec. 27, 1988

[54] IN SITU CONDUCTIVITY MONITORING TECHNIQUE FOR CHEMICAL/MECHANICAL PLANARIZATION ENDPOINT DETECTION

[75] Inventors: Carter W. Kaanta, Colchester; Michael A. Leach, Bristol, both of Vt.

[73] Assignee: IBM Corporation, Armonk, N.Y.

[21] Appl. No.: 147,422

[22] Filed: Jan. 25, 1988

[51] Int. Cl.⁴ .................... H01L 21/306; B44C 1/22
[52] U.S. Cl. ..................... 156/627; 156/636; 156/637; 156/645; 156/662; 156/345; 156/903
[58] Field of Search ............... 156/626, 627, 636, 637, 156/639, 645, 662, 903, 345; 51/281 R, 317

[56] References Cited

U.S. PATENT DOCUMENTS

| | | | |
|---|---|---|---|
| 3,063,206 | 11/1982 | Meyerhoff | 51/161 |
| 3,874,959 | 4/1975 | Hoekstra et al. | 156/345 X |
| 4,197,676 | 4/1980 | Sauerland | 51/165 R |
| 4,199,902 | 4/1980 | Sauerland | 51/165 R |
| 4,207,137 | 6/1980 | Tretola | 156/627 |
| 4,340,456 | 7/1982 | Robinson et al. | 156/627 X |
| 4,358,338 | 11/1982 | Downey et al. | 156/627 |
| 4,407,094 | 10/1983 | Bennett et al. | 51/165 R |
| 4,514,436 | 4/1985 | Moerschel | 156/627 X |
| 4,602,981 | 7/1986 | Chen et al. | 156/627 |
| 4,622,094 | 11/1986 | Otsubo | 156/627 |

OTHER PUBLICATIONS

IBM Technical Disclosure Bulletin, vol. 19, No. 4, Sep. 1976, by J. R. Skobern, "Nodule Removal Tool".

*Primary Examiner*—William A. Powell
*Attorney, Agent, or Firm*—Sughrue, Mion, Zinn, Macpeak & Seas

[57] ABSTRACT

An apparatus and method for monitoring the conductivity of a semiconductor wafer during the course of a polishing process. A polishing pad that contacts the wafer has an active electrode and at least one passive electrode, both of which are embedded in the polishing pad. A detecting device is connected to the active and passive electrodes for monitoring the current between the electrodes as the wafer is lapped by the polishing pad. The etch endpoint of the wafer is determined as a function of the magnitude of the current flow.

18 Claims, 3 Drawing Sheets

IN SITU CONDUCTIVITY MONITORING TECHNIQUE FOR CHEMICAL/MECHANICAL PLANARIZATION ENDPOINT DETECTION

FIELD OF THE INVENTION

This invention relates to an apparatus and method for determining an etch endpoint, during a chemical/mechanical lapping process, of a semiconductor wafer.

BACKGROUND OF THE INVENTION

Presently, there are various types of lapping machines for reducing the thickness of semiconductor wafers. In general, these lapping machines include top and bottom lapping plates, between which the wafers are positioned. The two lapping plates are then moved relative to each other, and a slurry, consisting of an abrasive solution with or without an etching reagent, is fed between the plates to grind and flush away the wafer particles. An example of such a lapping machine is disclosed in U.S. Pat. No. 3,063,206.

U.S. Pat. Nos. 4,197,676 and 4,199,902 each disclose a lapping machine for automatically controlling the lapping of piezoelectric wafers. The top plate of the lapping machine includes an electrode having a solid dielectric disk, an upper conducting surface and a conducting rod or wire connected to the conducting surface. The lapping machine further includes a voltage-controlled oscillator whose output is connected to a resistor which is in series with the electrode, an automatic control circuit, a sweep voltage terminal, a solid state relay connected in series with a lapping machine motor, and a power line outlet connected to the control circuit. The automatic feature of the lapping machine serves to terminate the lapping process when the frequency of one or more of the piezoelectric wafers reaches a defined relationship with a target frequency. U.S. Pat. No. 4,199,902 includes an embodiment wherein a second electrode is embedded in the top plate.

U.S. Pat. No. 4,407,094 also discloses a lapping machine for automatically controlling the lapping of a semiconductor wafer. The machine includes a pin diode having two terminals. One of the terminals is connected to an electrode which is inserted into a lapping plate, and the other terminal is connected to a sweep frequency generator. Each of the two terminals is also connected to an impedance comparator which senses the presence or absence of a piezoelectric wafer under the electrode, and which actuates a switch connected to an automatic control circuit. The control circuit serves to sense wafer frequencies, and to control a relay which switches between a lapping motor and a power supply. In operation, the lapping machine monitors the resonance frequency of a wafer, compares the resonance frequency with a predetermined target frequency, and activates a relay when the wafer frequency equals or exceeds the target frequency.

IBM Technical Disclosure Bulletin, Vol. 19, No. 4, Sept. 1976, by J. R. Skobern, discloses an electrical removal technique for removing metal nodules which penetrate an insulative layer of an electronic system. The technique includes placing a conductive "commoning ring" over the metal layer, and connecting the ring to the ground terminal of a power supply. The technique further includes placing a metal plate in contact with the metal nodules, and connecting the plate to the positive terminal of the power supply. When the power supply is activated, the metal nodules are subjected to high current density, thereby causing the nodules to vaporize.

In addition to lapping machines, various other devices and methods exist for determining etch endpoints of semiconductor wafers. The following are examples of such devices and methods.

U.S. Pat. No. 3,874,959 discloses an apparatus for detecting the etch endpoint of an oxide coated semiconductor substrate. The apparatus includes a first electrical lead wire connected to the substrate, and a second electrical wire connected to an electrode disposed in a bath of etching solution. The lead wires are connected to a detector or readout meter. A d.c. light source is focused on the substrate to provide a spot of light at the etching point. As the oxide coating of the semiconductor substrate is etched away, a signal is detected when the etching solution makes electrical contact with the material of the semiconductor substrate.

U.S. Pat. No. 4,207,137 discloses a plasma endpoint etching process which includes placing a semiconductor body between two electrodes, and supplying power to the electrodes so that a plasma is created for etching the semiconductor body. The plasma etch endpoint is determined by monitoring the impedance of the plasma during the etching process.

U.S. Pat. No. 4,602,981 discloses a method of determining the endpoint of a plasma etching process by measuring the RF voltage at an electrode. The method includes placing upper and lower electrodes on opposite surfaces of a wafer, connecting the upper electrode to ground, and connecting the lower electrode to an RF source through a matching impedance to measure the RF voltage.

U.S. Pat. Nos. 4,340,456 and 4,358,338 are cited as examples of etch endpoint detection techniques for plasma etching.

In VLSI wiring technology, connecting metal lines are formed over a substrate containing device circuitry. These metal lines serve to electrically interconnect the discrete devices. These metal connecting lines are insulated from the next interconnection level by thin films of insulating material formed by, for example, chemical vapor deposition (CVD) of oxide. In order to interconnect metal lines of different interconnection levels, holes are formed in the insulating layers to provide electrical access therebetween.

In such wiring processes, it is desirable that the insulating layers have a smooth surface topography, because rough surfaces cause fabrication problems. More specifically, it is difficult to image and pattern layers applied to rough surfaces, and this difficulty increases as the number of layers increases.

A recent development in the art is the use of lapping machines and other chemical/mechanical planarization processes to provide smooth insulator topologies for the next metal level. In these processes, it is important to remove a sufficient amount of material to provide a smooth surface, without removing an excessive amount of underlaying materials. Thus, a precise etch endpoint detection technique is needed.

Traditionally, lasers and other optical detection devices have been employed to determine etch endpoint. However, the design of such optical devices is difficult to implement in lapping machines, because the wafers are polished face down against a spinning wheel in such machines. More particularly, the wafer is hidden under a wafer holder and template, thereby making optical endpoint detection difficult.

The usual method employed for determining endpoint in lapping machines is to measure the amount of time needed to planarize the first wafer, and then to run the remaining wafers at similar times. In practice, because it is extremely difficult to precisely control the rate of film removal for different wafers, this method is extremely time consuming since operators must inspect each wafer after polish.

Thus, there remains a continuing need in the semiconductor fabrication art for an apparatus and method which accurately and efficiently detects the endpoint of a lapping planarization process.

SUMMARY OF THE INVENTION

It is thus an object of the present invention to provide an apparatus and method which accurately and efficiently detects the endpoint of a lapping planarization process.

This and other objects are realized in the present invention which provides an apparatus and method for electrically determining the etch endpoint of a semiconductor wafer. The apparatus comprises: a plurality of isolated electrode means coupled to the lapping machine, at least one of said plurality of isolated electrode means contacting a surface of the workpiece; and means for monitoring current flow between said plurality of isolated electrode means, said current indicating the amount of conductive material at the exposed surface of the substrate. The method comprises: mechanically planarizing the wafer with a polishing pad; forming an active and at least one passive electrode in said polishing pad; and electrically detecting either the presence or absence of the conductive portion of the semiconductor wafer.

PREFERRED EMBODIMENTS OF THE INVENTION

Figure 1:
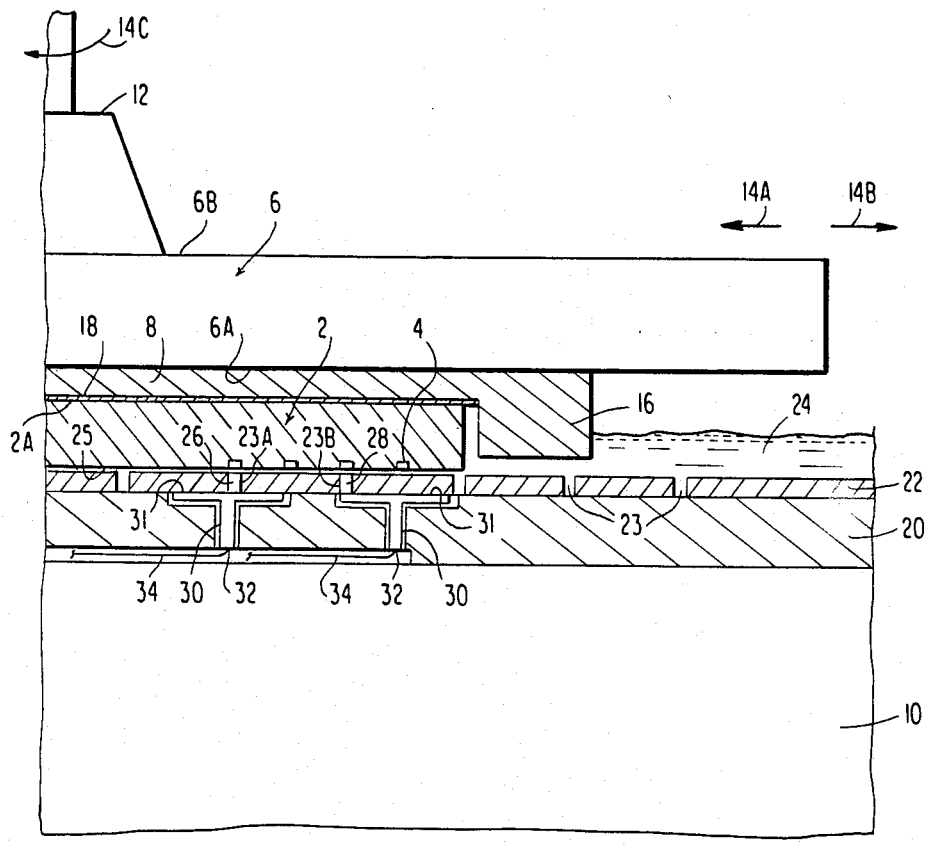
FIG. 1 is a simplified cross-sectional diagram of a lapping machine according to an embodiment of the invention.

FIG. 1 shows an apparatus for chem/mech polishing a semiconductor wafer 2 having metal lines, contact/via studs, and/or pads 4 according to a first embodiment of the invention. The apparatus includes a wafer carrier or holder 6 having a template 8 fixed to one side 6A thereof. The semiconductor wafer 2, which is to be processed in accordance with the invention, is shown positioned between the wafer carrier 6 and a polishing table 10. The wafer carrier 6 is coupled, at its other side 6B, to a driving arm 12. The arm 12 is coupled to any suitable motor or driving means (not shown) for moving the wafer carrier 6 in the directions indicated by arrows 14A, 14B, and 14C (rotation). The template 8 includes an edge portion 16 which prevents the wafer 2 from sliding out from under the wafer carrier 6 as the carrier moves. Attached to the template is an insert 18, which is preferably made from a soft material so that the wafer surface 2A is not damaged from the weight of the carrier 6. The polishing table 10 includes a platen 20 and a polishing pad 22 having holes 23 formed therein. Active and passive electrodes 26 and 28, respectively, are formed in the perforated polishing pad 22 by filling in some holes such as 23A and 23B of the pad 22 with a conductive epoxy material or the like. The platen 20 includes two insulated contacts 30, each having an upper conductive portion 31 and a lower conductive portion 32. The upper conductive portion 31 is positioned to contact the epoxy material, and the lower conductive portion 32 is positioned to contact conducting wires 34.

Figure 2:
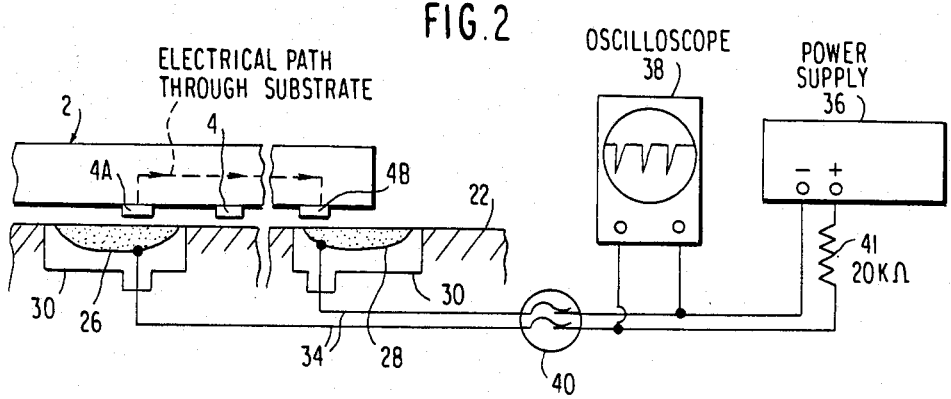
FIG. 2 is a schematic circuit diagram of the embodiment of FIG. 1.

In FIG. 2, the active and passive electrodes 26 and 28, respectively, are each shown connected to a power supply 36 and to a storage oscilloscope or other suitable electronics 38 through a slip ring assembly 40. The active electrode 26 is connected to the positive terminal of the power supply 36 through the slip ring assembly 40 and through a resistor 41. The passive electrode 28 is connected to the negative terminal of the power supply 36 through the slip ring assembly 40. The power supply 36 is designed to generate a bias voltage of 0.4 V, and resistor 41 has a resistance, for example, of 450KΩ to limit the current (20 μamps) supplied to the active electrode 26.

The operation of the embodiment of FIG. 2 will now be described.

At the beginning of the planarization or polishing process, wafer 2 is covered with a layer of insulating material such as silicon dioxide. Since electrodes 26 and 28 initially contact only the insulating layer, an open circuit results. As the planarization process proceeds, the insulating layer is removed, exposing grounded or substrate contacting metal pads 4. When electrodes 26 and 28 both contact the exposed pads 4, a current path is formed through the substrate of the wafer 2.

More specifically, a 20 μamp current flows from metal 4A (which is in contact with electrode 26) to metal 4B (which is connected to electrode 28) through the interconnecting wiring and circuitry formed in the substrate of wafer 2. As the wafer passes over the electrode pulses or spikes appear on the screen of oscilloscope 38. The current supplied to electrode 26 is limited to 20 μamps to prevent damage to the underlying circuitry. The pulses appearing on the screen of oscilloscope 38 indicate that the polish endpoint of the wafer 2 has occurred (e.g. metal points 4 are exposed). Those skilled in the art will understand that, in an automatic system, these pulses can be electrically integrated to trigger the lapping machine to stop the process or alternatively to start a sequencer to provide a desired over polish or percentage beyond end point, and then terminate the process.

Figure 3:
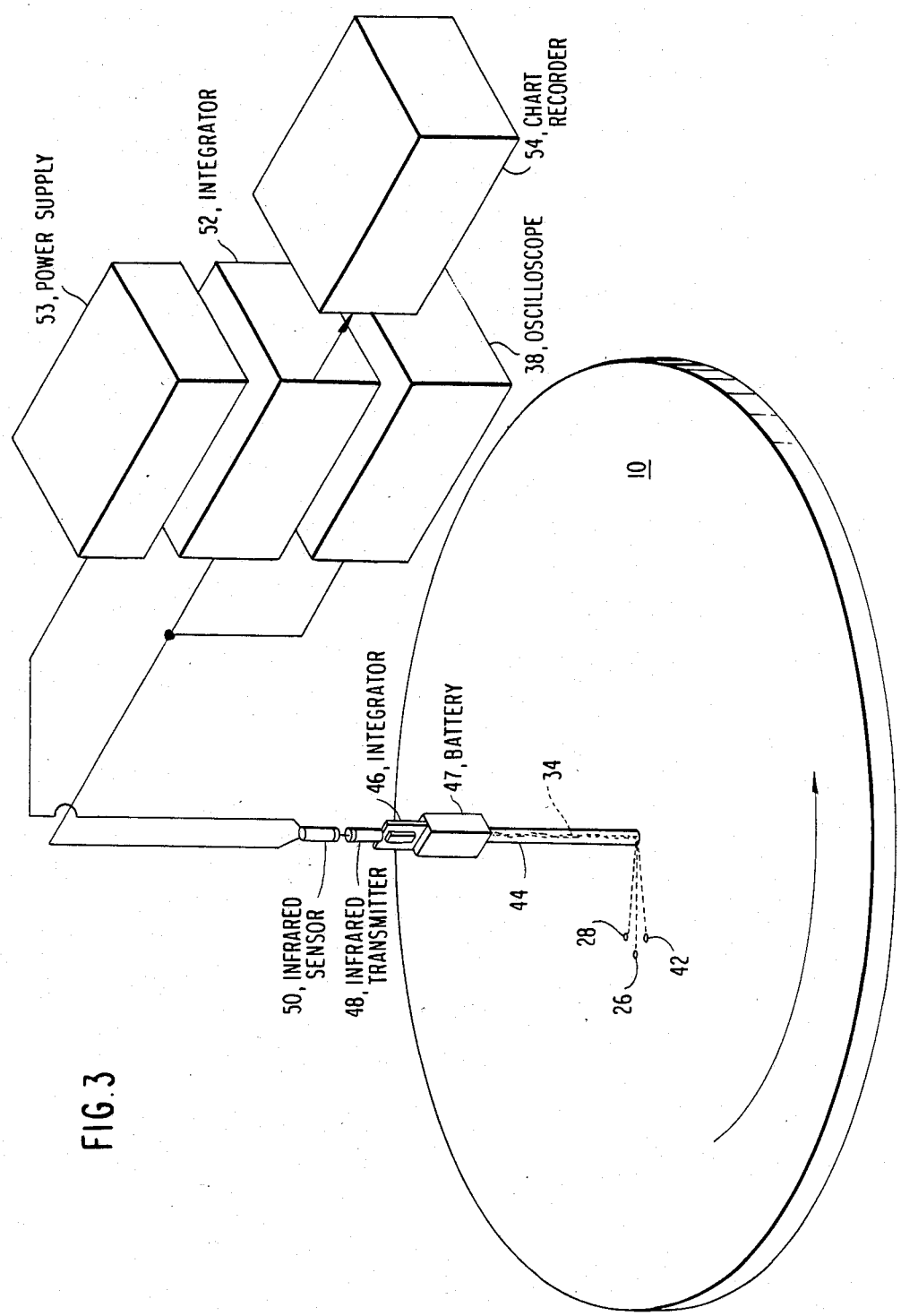
FIG. 3 is a perspective view of a lapping machine having a three electrode triangular arrangement according to a second embodiment of the invention.

In FIG. 3, a second preferred embodiment of the invention is shown, wherein three electrodes 26, 28 and 42 are disposed in a triangular manner in the polish pad so that a current path through the semiconductor wafer occurs only if all of the electrodes 26, 28 and 42 make simultaneous contact with exposed metal.

This three electrode triangular arrangement obviates the problem which occurs when some annual area polishes at a faster rate than the rest of the wafer. For example the edge of the semiconductor wafer maybe polished at a faster rate than the wafer center. When both electrodes of a two electrode arrangement contact exposed metal pads or lines located near the edges of the wafer, a false endpoint will result. By arranging the electrodes in a triangular form, and by requiring that all of the electrodes make contact before an etch endpoint is indicated, the problem of early etch endpoint is obviated.

More specifically, the three electrodes are positioned such that, even if two electrodes make electrical contact with exposed metal located at the edge of the wafer, an etch endpoint will not be indicated until the third electrode site is exposed by further polishing.

In FIG. 3, the three electrodes 26, 28 and 42 are shown embedded in polishing table 10. A tube 44 is positioned to carry electrical wires 34 to an integrator 46 which is coupled to a 9 V battery 47. The integrator 46 is coupled to an infrared transmitter 48. The transmitter 48 generates an infrared beam when all of the electrodes 26, 28 and 42 make contact with exposed metal located within the semiconductor wafer. An infrared sensor 50 serves to detect the generated infrared beam and, in response thereto, to transmit an electrical signal to a second integrator 52. The integrator 52 is coupled to oscilloscope 38, to chart recorder 54, and to power supply 53. The oscilloscope 38 displays signals or pulses when an etch endpoint has occurred, and the chart recorder 54 records spikes representing an integrated etch endpoint when the integrator 52 produces a specific output.

Figure 4:
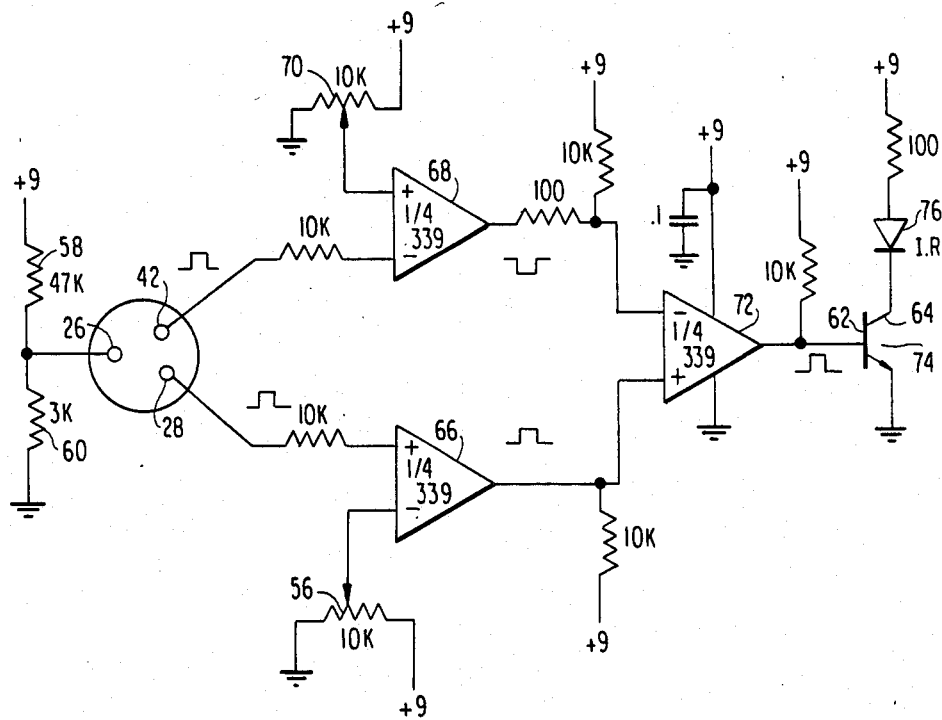
FIG. 4 is a circuit diagram of a comparator circuit according to the embodiment of FIG. 3.

In FIG. 4, there is shown the circuit arrangement of the integrator 46 of FIG. 3. Electrode 26 is connected to a small current source formed by resistors 58 and 60 and a 9 V voltage supply (e.g. battery 47 in FIG. 3). The electrodes 28 and 42 are connected to the positive and negative terminals of comparators 66 and 68, respectively. Offset adjust circuits 56 and 70 are each formed by a variable 10KΩ resistor and a 9 V voltage supply. Circuits 70 and 56 are each connected to the positive and negative terminals of comparators 68 and 66, respectively. The output of comparator 68 is connected to the negative terminal of a comparator 72, and the output of comparator 66 is connected to the positive terminal of comparator 72. The output of comparator 72 is coupled to the base region 62 of a transistor 74. An infrared diode with a 100Ω current limiting resistor 76 is coupled to the collector region 64 of transistor 74. A small current source formed by a 10KΩ resistor and a 9 V voltage supply, is connected to the base region of transistor 74. The emitter 74 is connected to ground.

The operation of the integrator circuit 46 of FIG. 4 will now be described with reference to the logic diagram of FIG. 5.

The integrator circuit 46 allows an infrared beam to be transmitted when all of the electrodes 26, 28 and 42 make electrical contact with an exposed metal pad or line within the wafer. When such electrical contact occurs, a current flows from active electrode 26 to passive electrodes 28 and 42 through the substrate. As a result, an electrical signal is sent to the positive and negative comparators 66 and 68.

The comparators 66 and 68 produces "HIGH" and "LOW" signal or pulse outputs respectively when the voltage at the input terminal is beyond a specified threshold value. The specified threshold value is set by adjusting the variable resistors of offset circuits 56 and 70. More particularly, the value of the threshold voltage is set as to offset small input currents, which may, for example, represent a current path from electrode 26 to electrodes 28 or 42 when using slightly conductive slurry solutions 24 (FIG. 1).

Figure 5:
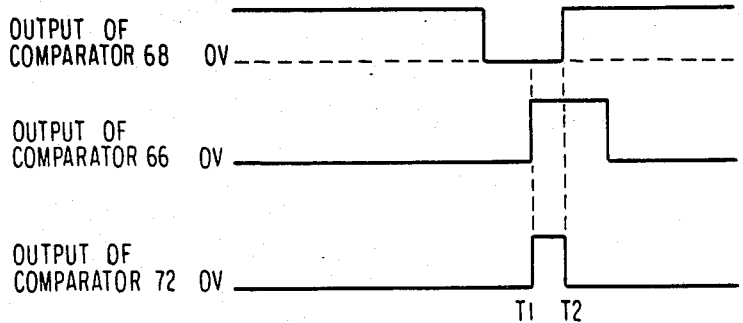
FIG. 5 is a logic diagram showing the operation of the integrator circuit of FIG. 4.

Comparator 72 produces an output pulse when both the output of comparator 68 produces a "LOW" signal, and comparator 66 produces a "HIGH" signal, as shown in the logic diagram of FIG. 5. As a result, the infrared transmitted 48 will generate infrared beam only when comparator 68 produces a "LOW" signal and comparator 66 produces a "HIGH" signal, (i.e. as shown in FIG. 5 between times T1 and T2). The generated infrared beam will then be sensed by an infrared receiver 50 and displayed by the oscilloscope 38 and the chart recorder 54 as indicated in FIG. 3.

While the invention has been described with reference to detecting etch endpoint of an insulating layer, it can also be applied to detecting etch endpoint of a conductive layer. In this application, the conducting path is broken at etch endpoint.

As described above, the endpoint detection system of the invention provides an indication of endpoint by monitoring the presence or absence of current between the active and passive electrodes. However, the invention can also be used to monitor the resistivity of a conductive layer during the polishing process. For example, this thinning of a conductive layer may be necessary to reduce the thickness of a CVD-deposited metal film. The CVD-metal may have been deliberately deposited thick to completely fill contact or via studs. The process would be used to reduce the metal thickness to its desired value by measuring sheet resistance during the polishing process.

Many structural modifications can be made to the endpoint detection system of the invention. While embodiments featuring two or three electrodes were disclosed, additional electrodes could be provided to enhance the accuracy of the system. The electrodes could be provided to portions of the lapping machine other than the polish pad. For example, one of the electrodes could be provided on the wafer support that contacts the backside of the wafer, such that during the lapping process a circuit is formed from the electrode on the polish pad, through the substrate, and to the electrode on the backside of the wafer. Moreover, if the slurry was conductive (ionic) the slurry becomes the front side (i.e., the polish pad) electrode, and the slurry could be held at a predetermined voltage by a biasing means coupled to the slurry. Finally, the electrodes could be made from conductive materials such as silver paint, copper braids, or graphite, or aluminum foil.

We claim:

1. An apparatus for monitoring the conductivity of an exposed surface of a workpiece during polishing in a lapping machine, comprising:
   a plurality of isolated electrode means coupled to the lapping machine, at least one of said plurality of isolated electrode means contacting a surface of the workpiece; and
   means for monitoring current flow between said plurality of isolated electrode means, said current indicating the amount of conductive material at the exposed surface of the substrate.

2. The apparatus according to claim 1, wherein the lapping machine comprises a polishing table, a polishing pad coupled to said polishing table, and a spinning wafer carrier suspended above said polishing table for bringing the workpiece into contact with said polishing pad.

3. The apparatus according to claim 2, wherein said plurality of isolated electrode means are embedded in said polishing pad.

4. The apparatus according to claim 3, wherein said plurality of isolated electrode means are provided by perforations in said polishing pad that are filled with conductive material.

5. The apparatus according to claim 3, wherein said plurality of isolated electrode means comprise a conductive material is selected from the group consisting of conductive epoxy, silver, graphite, copper, and aluminum.

6. The apparatus according to claim 2, wherein said plurality of isolated electrode means comprise first, second, and third electrodes embedded in said polishing pad.

7. The apparatus according to claim 6, wherein said means for monitoring current flow comprises:
a first comparator coupled to said second electrode, said first comparator producing a first signal that indicates the presence of current flow between said first and second electrodes;
a second comparator coupled to said third electrode, said second comparator producing a second signal that indicates the presence of current flow between said first and third electrodes, and;
a third comparator coupled to said first and second comparators for detecting the simultaneous presence of said first and second signals.

8. The apparatus according to claim 7, wherein said electrodes are arranged in a triangular manner in said polishing pad.

9. An apparatus for determining an etch endpoint, during a lapping process, of a work piece having at least one conductive portion and at least one insulative portion, comprising:
means for planarizing the work piece;
an active electrode and at least one passive elecrode, both of which are coupled to said planarizing means; and
means, coupled to said active and said at least one passive electrode, for electrically detecting when said active and passive electrodes contact the conductive portion of the work piece, whereby the etch endpoint of the work piece is determined by monitoring an output of said detecting means.

10. The apparatus according to claim 9, wherein said planarizing means comprises a polishing table having a polishing pad disposed thereon.

11. The apparatus according to claim 10, wherein said polishing table has a platen for supporting said polishing pad.

12. The apparatus according to claim 10, wherein said active electrode and said at least one passive electrode are embedded in said polishing pad.

13. The apparatus according to claim 10, wherein said active electrode and said at least one passive electrode are defined by holes of said perforated polishing pad which are filled with conductive epoxy material.

14. The apparatus according to claim 11, further comprising insulated contacts located in said platen, said contacts having conductive portions for connecting said active electrode and said at least one passive electrode to said detecting means.

15. A polishing pad for controllably lapping a work piece having at least one insulative portion and at least one non-insulative portion, said pad comprising an insulative support structure having an active electrode and at least one passive electrode embedded therein, said active and passive electrodes contacting respective portions of the work piece, so that during the lapping process the existence of current flow through said passive electrode indicates that portions of the non-insulative portion of the work piece are in contact with both the active and passive electrodes of the polishing pad.

16. The apparatus according to claim 15, wherein said polishing pad has a plurality of perforations, selected ones of said perforations being at least partially filled with conductive material to provide said electrodes.

17. The apparatus according to claim 16, wherein said conductive material is selected from the group consisting of conductive epoxy, silver, graphite, and copper.

18. A method for monitoring the conductivity of a work piece during the course of a lapping process carried out in a lapping machine having a polishing pad that contacts the work piece, the polishing pad having an active electrode and at least one passive electrode contacting the work piece, comprising the step of:
monitoring the current flow between said active and at least one passive electrode of the polishing pad during the polishing process.

* * * * *